United States Patent [19]
Ahmed

[11] Patent Number: 5,743,869
[45] Date of Patent: Apr. 28, 1998

[54] MEDICAL DEVICE AND METHOD FOR TREATING ASCITES

[76] Inventor: Abdul Mateen Ahmed, 928 E. Juanita Ave., La Verne, Calif. 91750

[21] Appl. No.: 592,639

[22] Filed: Jan. 26, 1996

Related U.S. Application Data

[63] Continuation-in-part of Ser. No. 269,839, Jul. 1, 1994, Pat. No. 5,616,118, which is a continuation of Ser. No. 786,734, Oct. 1, 1991, Pat. No. 5,411,473, which is a division of Ser. No. 478,655, Feb. 12, 1990, Pat. No. 5,071,408, which is a continuation-in-part of Ser. No. 255,070, Oct. 7, 1988, abandoned.

[51] Int. Cl.$^6$ .................................................. A61M 5/00
[52] U.S. Cl. ......................................... 604/9; 604/8
[58] Field of Search ........................... 604/8, 9, 10, 185; 137/510

[56] References Cited

U.S. PATENT DOCUMENTS

| | | | |
|---|---|---|---|
| 3,654,932 | 4/1972 | Newkirk et al. | 604/9 |
| 3,827,439 | 8/1974 | Schulte et al. | 604/9 |
| 4,741,730 | 5/1988 | Dormandy, Jr. et al. | 604/9 X |
| 4,761,158 | 8/1988 | Schulte et al. | 604/9 |
| 4,850,955 | 7/1989 | Newkirk | 604/9 |

*Primary Examiner*—Sam Rimell
*Attorney, Agent, or Firm*—John J. Connors; Connors & Assocs.

[57] ABSTRACT

Disclosed is a medical device comprising an external, flexible shell forming a fluid chamber reservoir and housing a valve, having a folded membrane which forms a chamber with a slit-like opening. The inlet tube in communication with the chamber extends outwardly through an opening in the shell. The inlet tube has a free end with holes and rigid fins. The free end of the inlet tube in communication with abdomen. There is an outlet tube in communication with the reservoir. The outlet tube has a free end with holes. The free end of the outlet tube is in communication with the jugular vein of a patient. Also disclosed is a method of using this device to treat ascites.

29 Claims, 8 Drawing Sheets

MEDICAL DEVICE AND METHOD FOR TREATING ASCITES

RELATED PATENT APPLICATIONS

This application is a continuation-in-part application of U.S. Ser. No. 08/269,839, entitled "Uniquely Shaped Ophthalmological Device," filed Jul. 1, 1994 now U.S. Pat. No. 5,616,118, which is a continuation-in-part application of U.S. Ser. No. 07/786,734, entitled "Medical Valve," filed Oct. 1, 1991, now U.S. Pat. No. 5,411,473, which is a divisional application of U.S. Ser. No. 07/478,655, filed Feb. 12, 1990, and entitled "Medical Valve," now U.S. Pat. No. 5,071,408, which is a continuation-in-part application of U.S. patent application Ser. No. 07/255,070, entitled "Self-Regulating Pressure Control Glaucoma Valve," filed Oct. 7, 1988 now abandoned. All of these related applications are incorporated herein by reference and made a part of this application.

BACKGROUND OF THE INVENTION

1. Field of Invention

This invention relates to medical devices which are implanted in the human body, particular to a medical device used to treat ascites.

2. Background Discussion

"Ascites" is a diagnostic term meaning excess fluid in the peritoneal cavity or abdomen. It results from exudation of fluid either from the surface of the liver or from the surfaces of the gut and its mesentery. Ascites usually will develop only when outflow of blood from the liver into the inferior vena cava is blocked. This disease process is known as cirrhosis of the liver and it may occur secondary to alcoholism, ingestion of poisons, virus diseases, bacterial infections or for reasons of unknown causes. Whatever the causative factor, when the blood flow through the portal system of the liver is blocked it causes extremely high pressure in the liver sinusoid, which in turn causes fluid to weep from the surfaces of the liver, filling the peritoneal space. The weeping fluid is almost pure plasma, containing tremendous quantities of protein. The protein, because it causes a high osmotic pressure in the abdominal fluid, then pulls (by osmosis) additional fluid from the surfaces of the gut and mesentery. Left untreated, cirrhosis of the liver may result in death.

In U.S. Pat. No. 5,411,473, there is disclosed a valve (herein the Glaucoma Valve) used to treat glaucoma by allowing aqueous humor to flow from the intraocular chamber of the eye to relieve excess pressure. The glaucoma valve uses an elastic membrane under tension to form its own fluid retention chamber. A slit-like opening is along adjoining, overlapping edges of portions of the membrane. The membrane responds to slight changes in fluid pressure and expands or contracts to open or close the opening. When opened, the slit-like opening provides a wide open mouth with parted lips that allows for free flow of fluid through it without any substantial resistance to fluid flow. This feature substantially reduces the likelihood that the opening will be clogged by particulate matter.

SUMMARY OF THE INVENTION

Central to the medical device of this invention is the adoption of the Glaucoma Valve to treat ascites. Using the Glaucoma Valve avoids or minimizes clogging and also provides for self regulation of flow through the device. While this invention provides a medical device and method for treating ascites, the medical device may be used for other applications.

There are several features of this invention, no single one of which is solely responsible for its desirable attributes. Without limiting the scope of this invention as expressed by the claims, its more prominent features will now be discussed briefly. After considering this discussion, and particularly after reading the section of the application entitled "DETAILED DESCRIPTION OF THE PREFERRED EMBODIMENTS," one will understand how the features of this invention provide its benefits, which include the ability to self regulate drainage of fluid from abdominal cavity into the jugular vein and to ascertain when, whether, and where the device may have become blocked. The device is easy to manufacture, performs reliably, is easy to implant surgically in the human body, and will remain functional for the time required by the patient in which it is implanted.

The first feature of the medical device of this invention is that it is designed to treat a patient suffering from ascites. It includes a one-way directional flow valve having a membrane which forms a chamber with a slit-like opening. The membrane has an aperture therein, and it is folded to form the slit-like opening and the chamber. The membrane is maintained in tension by a pair of plates that are held together by means of a plurality of pins. This one-way flow device functions as a check valve to permit the flow of fluid in one direction only. This combined assembly will permit entry into the chamber of ascites fluid from the abdomen through the inlet tube and one-way flow valve. The valve is non-obstructive and self regulating, especially designed to include a venturi for automatic control of flow through the valve.

The second feature is a flexible shell which encloses the valve. The shell is injection molded from a polymeric material and it provides a reservoir with first and second ends, each of these ends having an opening therein. The shell expands or contracts in response to pressure within the reservoir. The valve prohibits the back flow of fluid from the reservoir into the valve and through the inlet tube and back into the abdomen. Because fluid may only flow in one direction through the valve, the drained fluid from the abdomen can only flow through the valve into the reservoir.

The third feature is an inlet tube in communication with the valve through the aperture. The inlet tube has an end portion received by the opening at the first end of the shell and connected through an aperture in the membrane to place the inlet tube in communication with the chamber within the valve. A free end of the inlet tube is adapted to be inserted into the patient's abdomen. This free end is open and has a plurality of holes adjacent it. At the free end there is a rigid fin structure. This fin structure is comprised of a plurality of fins adjacent to the opening at the tip of the inlet tube with the plurality of holes adjacent to the rigid fin structures. The purpose of the fin structure is to facilitate fluid drainage by helping to prevent the inlet tube from becoming clogged due to the growth of omentum from within the abdomen. Without this fin structure, omentum, which is floating matter that covers all inert tubing, may establish a residency upon the openings of the inlet tube and thereby prevent the drainage of fluid. The unique fin structure encourages the holes and openings within the free end to remain unblocked. The structure provides a site to collect omentum in an open structure that minimizes the possibility of blocking the drainage. Without this fin structure, omentum may establish a residency upon the openings of the tube and thereby prevent drainage of fluid.

The fourth feature is that the inlet tube has a telescoping component which has been adapted to elongate on demand. This feature is to accommodate the need for tubing which is

3 capable of lengthening without resorting to additional surgical procedures.

The fifth feature is an outlet tube in communication with the reservoir in the shell. The outlet tube has one end portion received by the opening at the second end of the shell, and a free end adapted to be inserted into the patient's jugular vein. The free end of the outlet tube is open and there may be a plurality of holes adjacent this open end. The placement of the free end into the jugular vein allows the collected ascites fluid to be discharged into the heart for absorption or excretion by the body of the patient.

The sixth feature is that this medical device may be used as a pump to maximizes the draining of ascites from the peritoneum, or for plural effusion.

The seventh feature of this invention provides a means for determining if the inlet or outlet tubes are obstructed. By manually pushing on the shell, the user will be able to ascertain whether or not the tubing is blocked. Further, the manner in which the flexible shell responds to manually applied pressure will inform the user as to whether the blockage is within the inlet tube or the outlet tube. If the device is clogged at the inlet tube, the fluid reservoir remains compressed after manual pressure has been removed. If the tubing is blocked within the outlet tube, the fluid reservoir resists compression and remains fully expanded.

This invention also includes a method for treating ascites by draining the fluid from the abdomen of a patient.

The method for treating ascites includes the steps of:

(a) providing a medical device, including
    a valve having a membrane which forms a slit-like opening, said membrane having an aperture therein,
    a flexible shell which encloses the valve, said shell having a reservoir and first and second ends, with said first and second ends having openings therein,
    an inlet tube in communication with the valve through the aperture, said inlet tube having an end portion received by the opening at the first end of the shell, and a free end adapted to be inserted in the abdomen, and
    an outlet tube in communication with the reservoir, said outlet tube having one end portion received by the opening at the second end of the shell, and a free end adapted to be inserted into the patient's jugular vein.

(b) attaching the medical device to the patient with the flexible shell facing outward, (c) inserting the free end of inlet tube into the abdomen to enable the ascites fluid to drain through the free end of the inlet tube, through the valve, and into the reservoir in the medical device, (d) inserting the free end of the outlet tube into the jugular vein of the patient to enable fluid to drain from the fluid reservoir into the heart.

BRIEF DESCRIPTION OF THE DRAWING

The preferred embodiment of this invention illustrating all of its features will now be discussed in detail. This embodiment depicts the novel and unobvious features of the medical device of this invention. The drawings accompanying this application, which is for illustrative purposes only, includes the following figures (FIG.), with like numerals indicating like parts.

4

Figure 2:
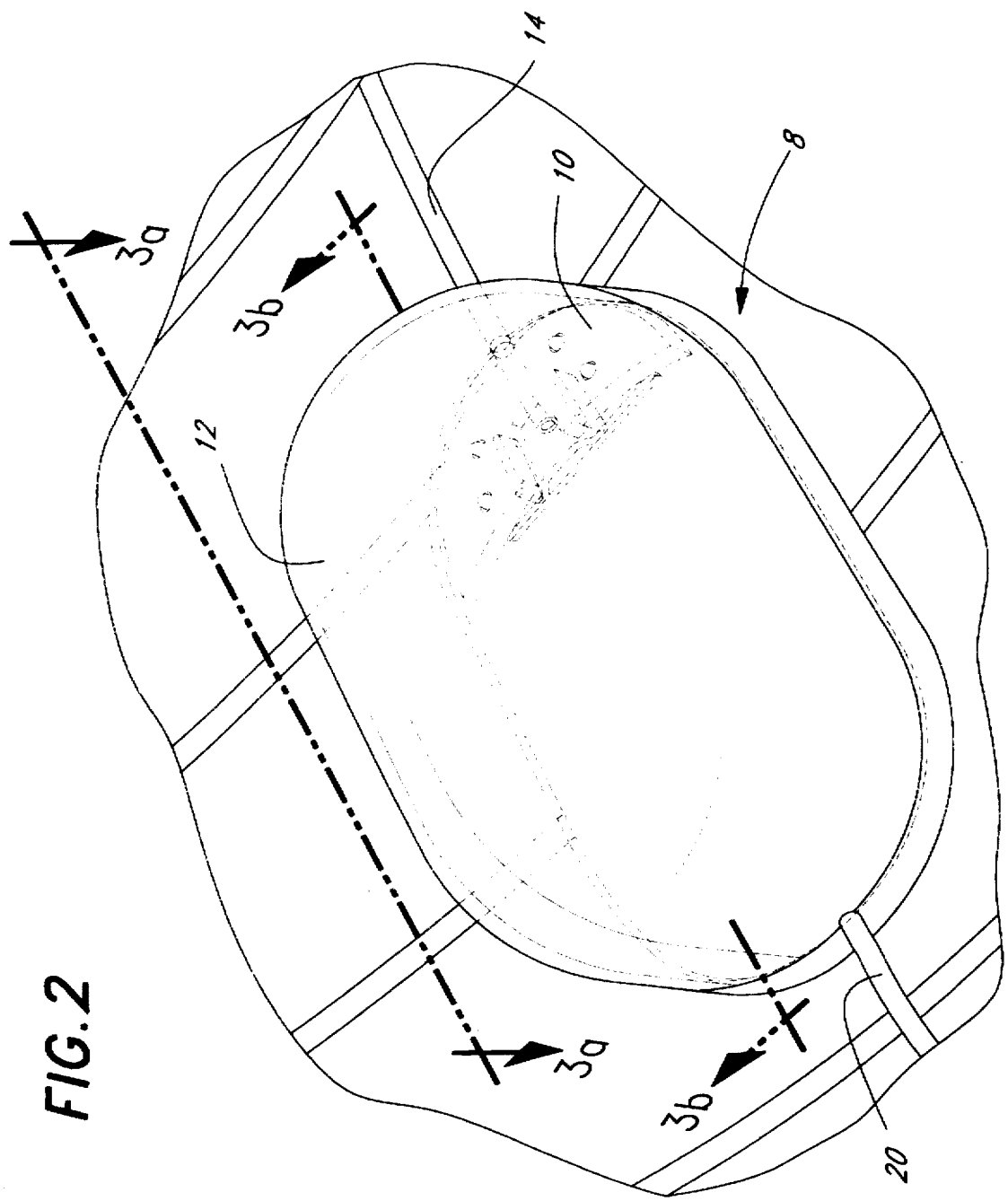

FIG. 2 is a perspective view of the medical device.

Figure 3A:
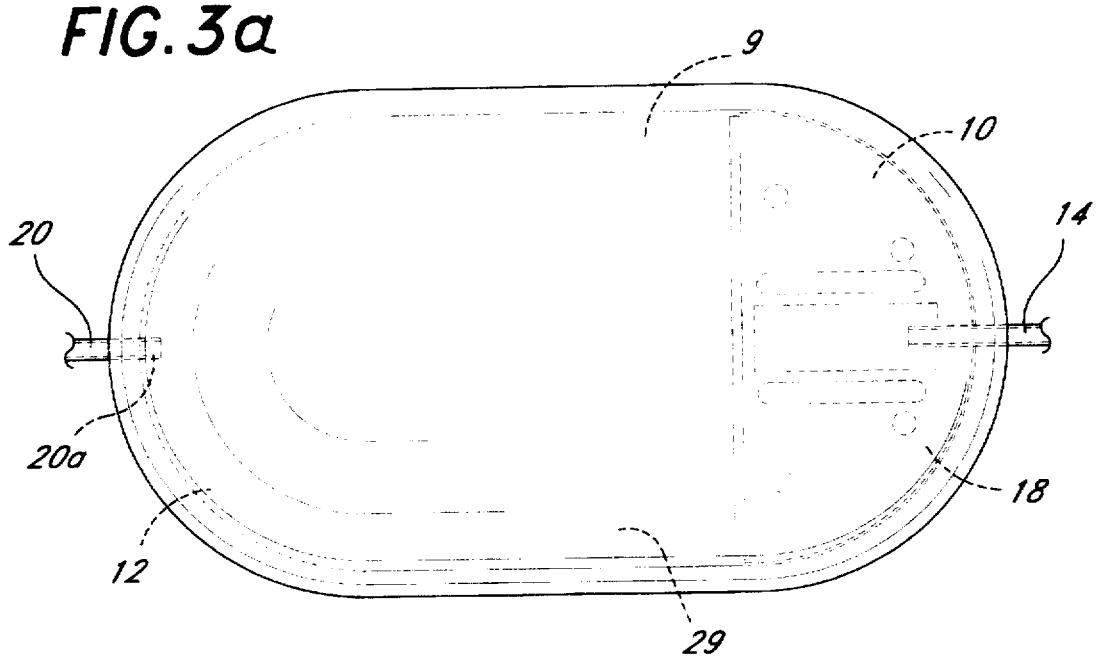

FIG. 3a is a plan view taken along line 3a—3a of FIG. 2.

Figure 3B:
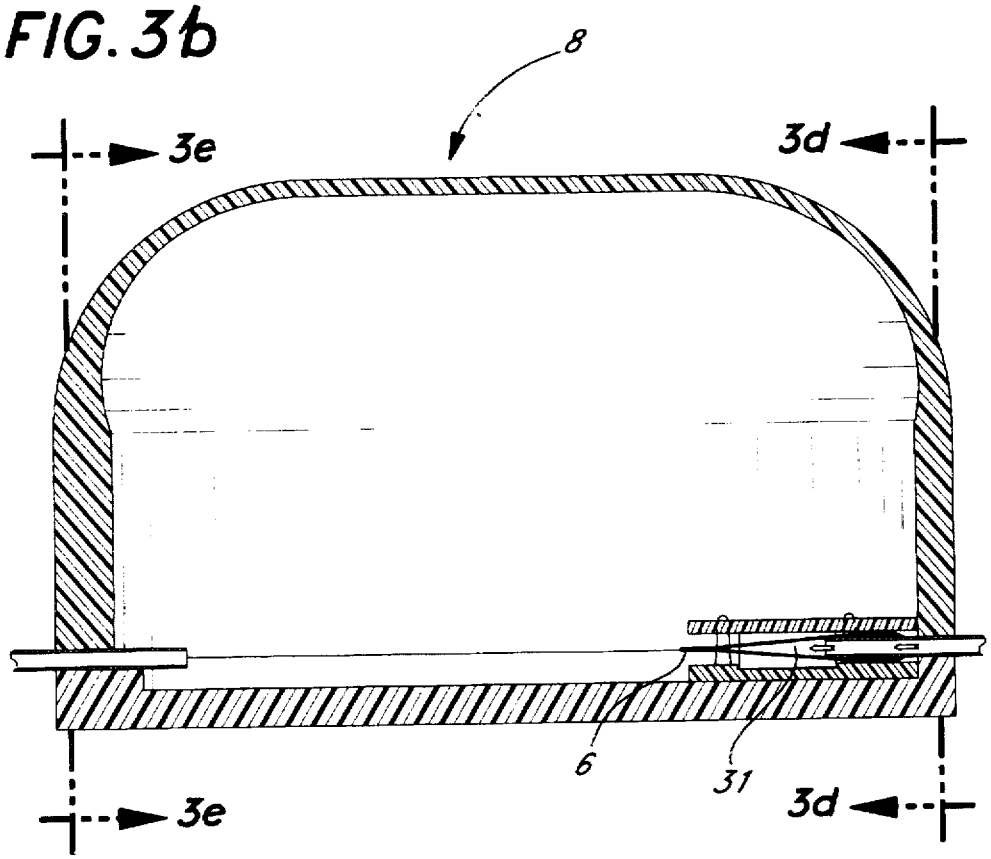

FIG. 3b is a cross-sectional view taken along line 3b—3b of FIG. 2.

Figure 3C:
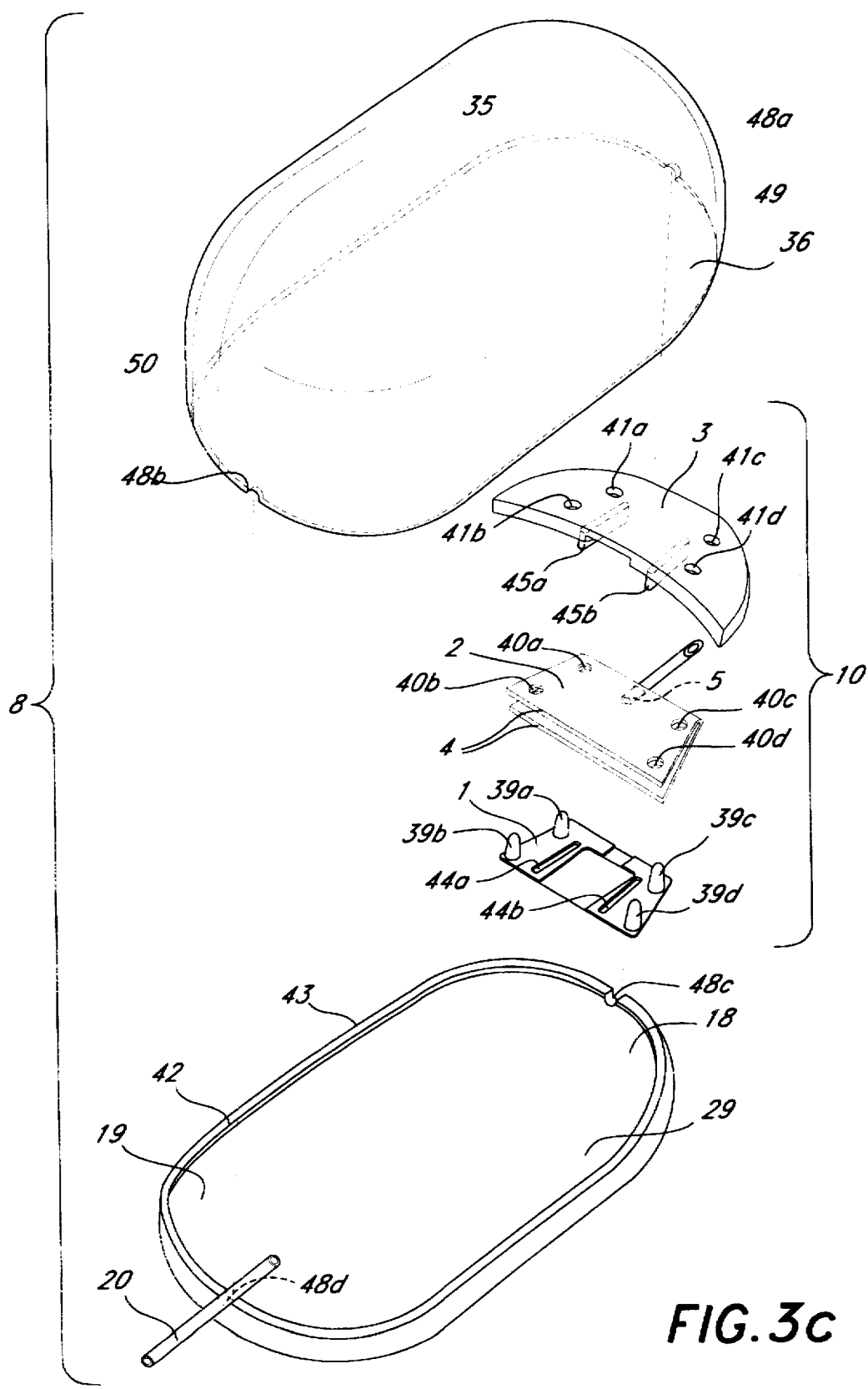

FIG. 3c is an exploded perspective view of the medical device of this invention.

Figure 3D:
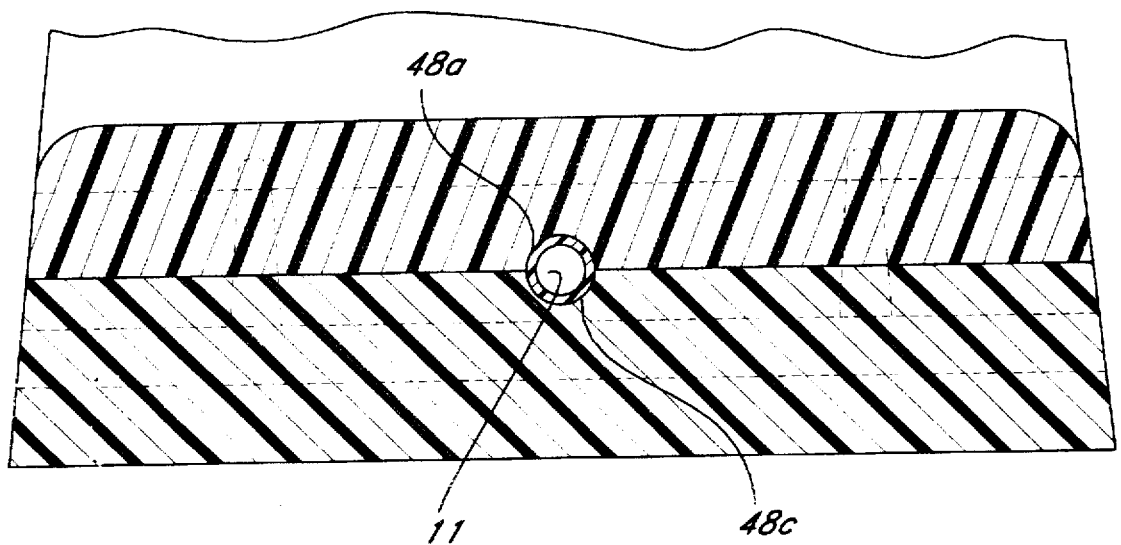

FIG. 3d is a cross-sectional view taken along line 3d—3d of FIG. 3b.

Figure 3E:
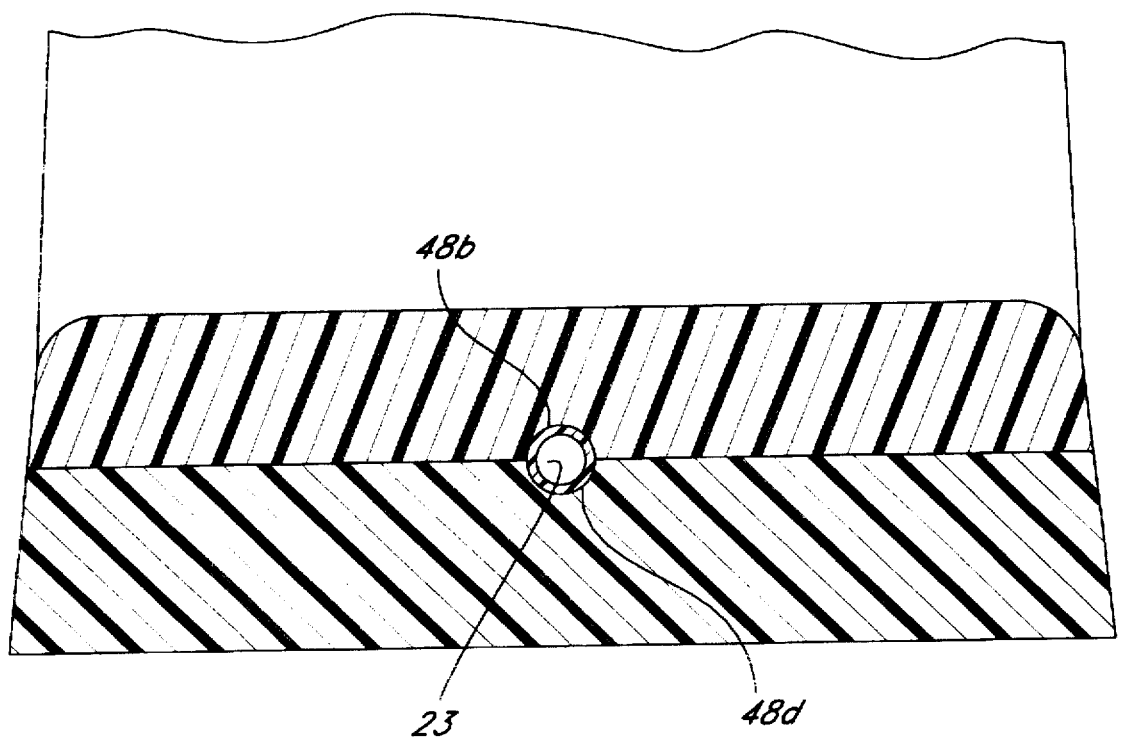

FIG. 3e is a cross-sectional view taken along line 3e—3e of FIG. 3b.

Figure 4A:
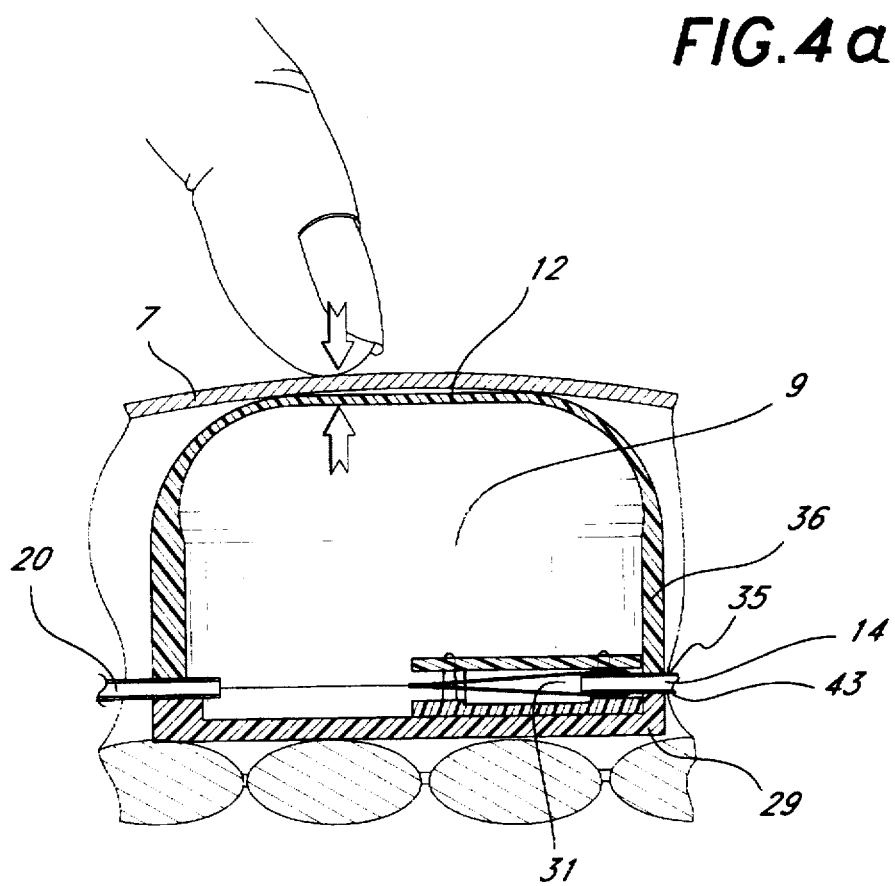

FIG. 4a is a cross-sectional view showing resistance of the shell to manual compression of the filled reservoir when there is an obstruction in the outlet robe.

Figure 4B:
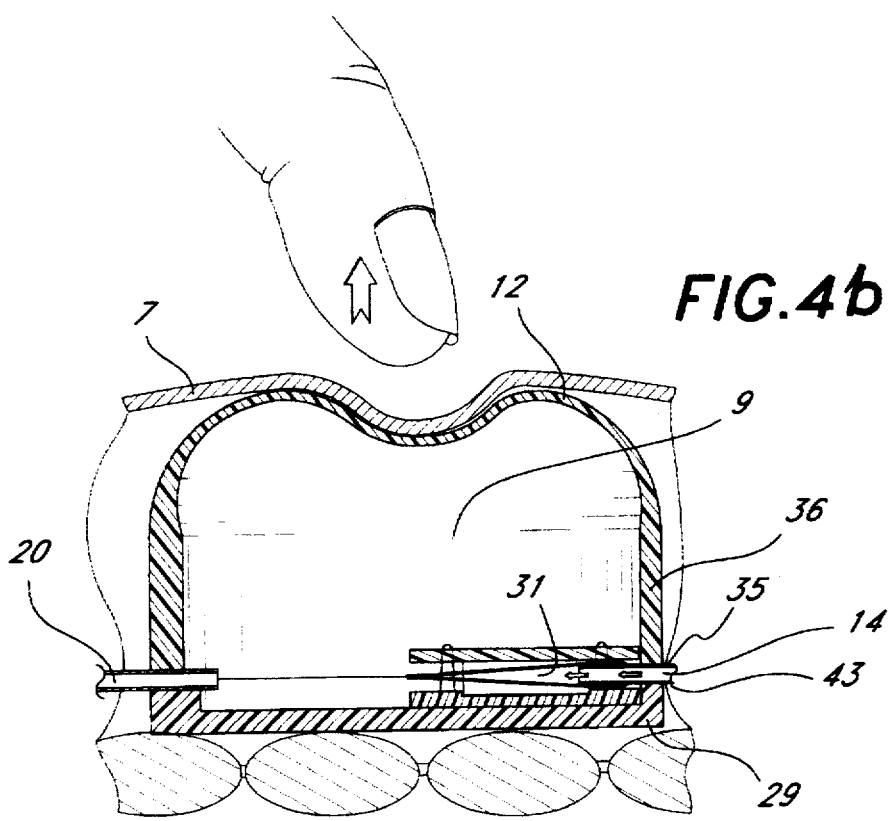

FIG. 4b is a cross-sectional view similar to that shown in FIG. 4a showing the shell remaining in the contracted position and appearing as a dimple in the skin which indicates an obstruction in the inlet line.

Figure 4C:
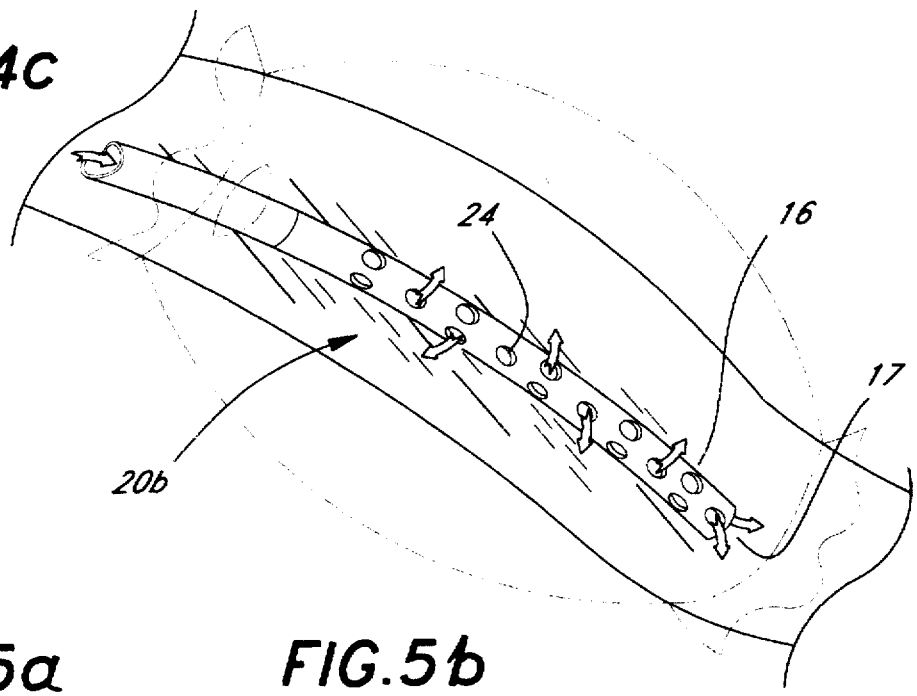

FIG. 4c is a fragmentary, perspective view of the end of the outlet tube inserted into the jugular vein of the patient.

Figure 5A:
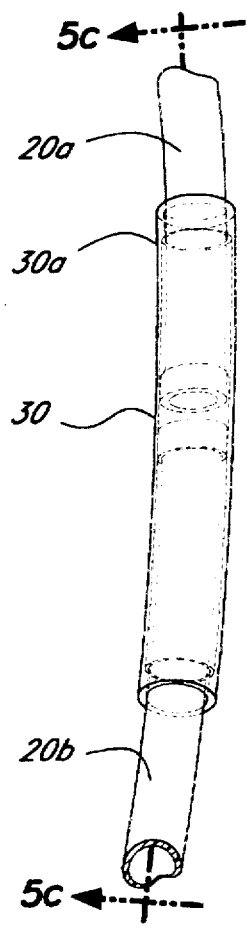

FIG. 5a is a perspective view of a portion of the inlet tube showing a telescoping feature with the inlet tube compressed.

Figure 5B:
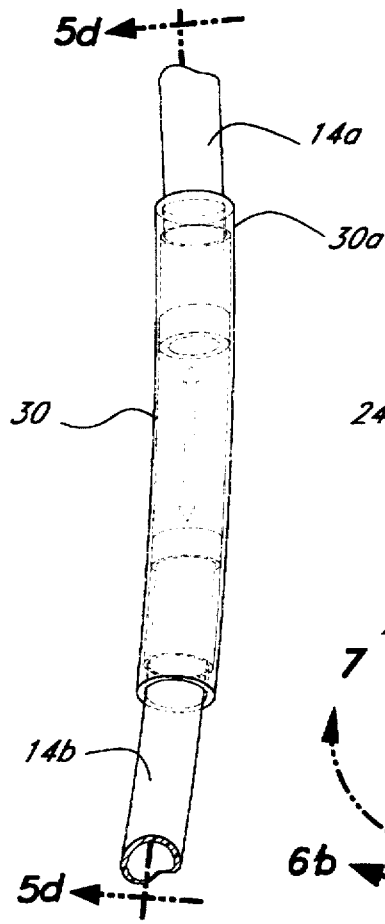

FIG. 5b is a perspective view similar to FIG. 5a showing the telescoping feature of the inlet tube when the inlet tube is expanded.

Figure 5C:
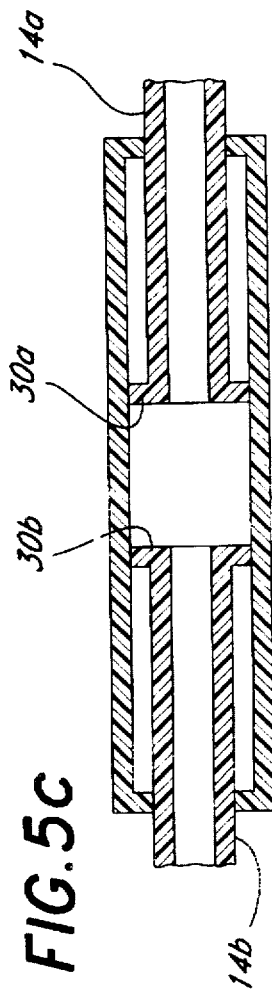

FIG. 5c is a cross-sectional view taken along line 5c—5c of FIG. 5b.

Figure 5D:
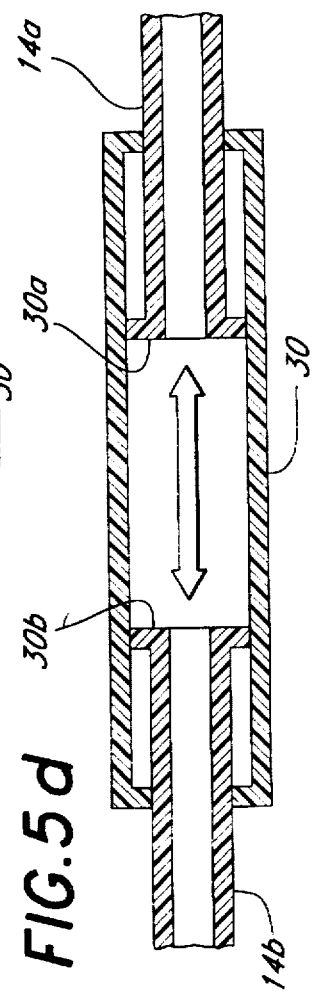

FIG. 5d is a cross-sectional view taken along line 5d—5d of FIG. 5b.

Figure 6A:
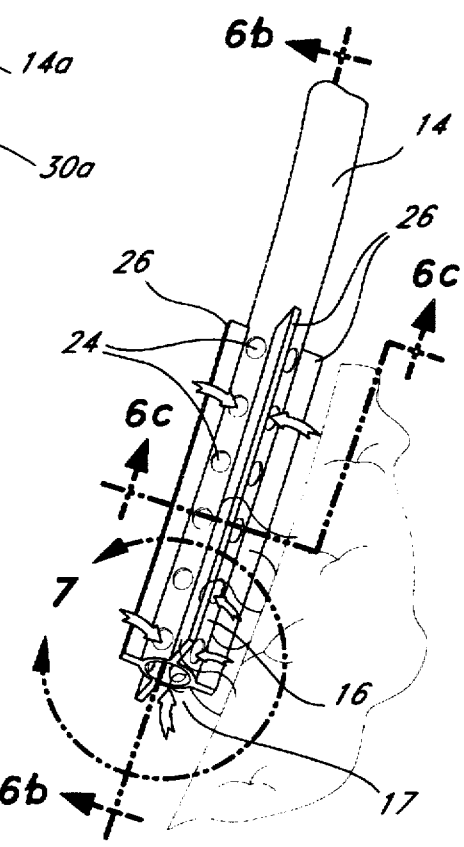

FIG. 6a is a fragmentary, perspective view showing free end of the inlet tube with the rigid fin structure placed in the abdomen.

Figure 6B:
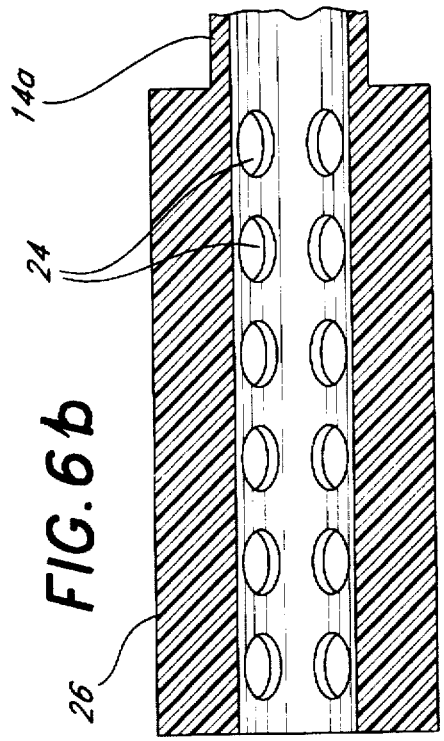

FIG. 6b is a cross-sectional view taken along line 6b—6b of FIG. 6a.

Figure 6D:
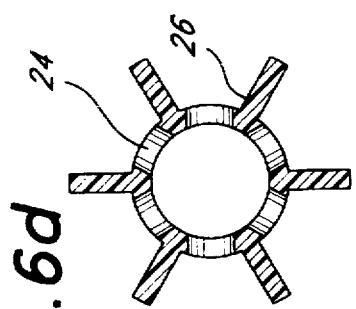
Figure 6C:
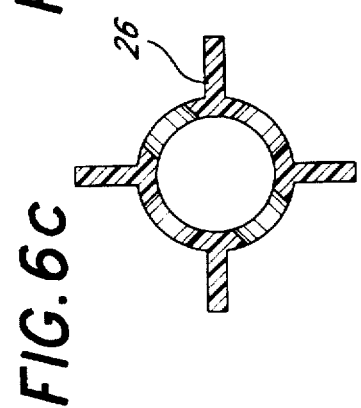

FIG. 6c is a cross-sectional view of the rigid fin structure taken along line 6c—6c of FIG. 6a.

FIG. 6d is a cross-sectional view of an alternate rigid fin structure for the end of the inlet tube.

Figure 7:
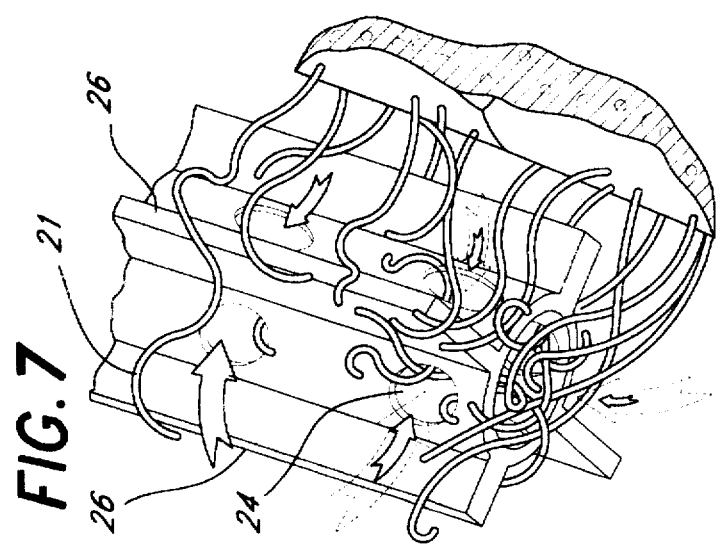

FIG. 7 is a perspective view showing the rigid fin structure at the free end of the inlet tube which prevents the omentum from blocking the inward flow of fluid through the opening and holes.

FIG. 8 is a schematic drawing illustrating the flow characteristics of the valve used in this invention.

DETAILED DESCRIPTION OF THE PREFERRED EMBODIMENT

Figure 1:
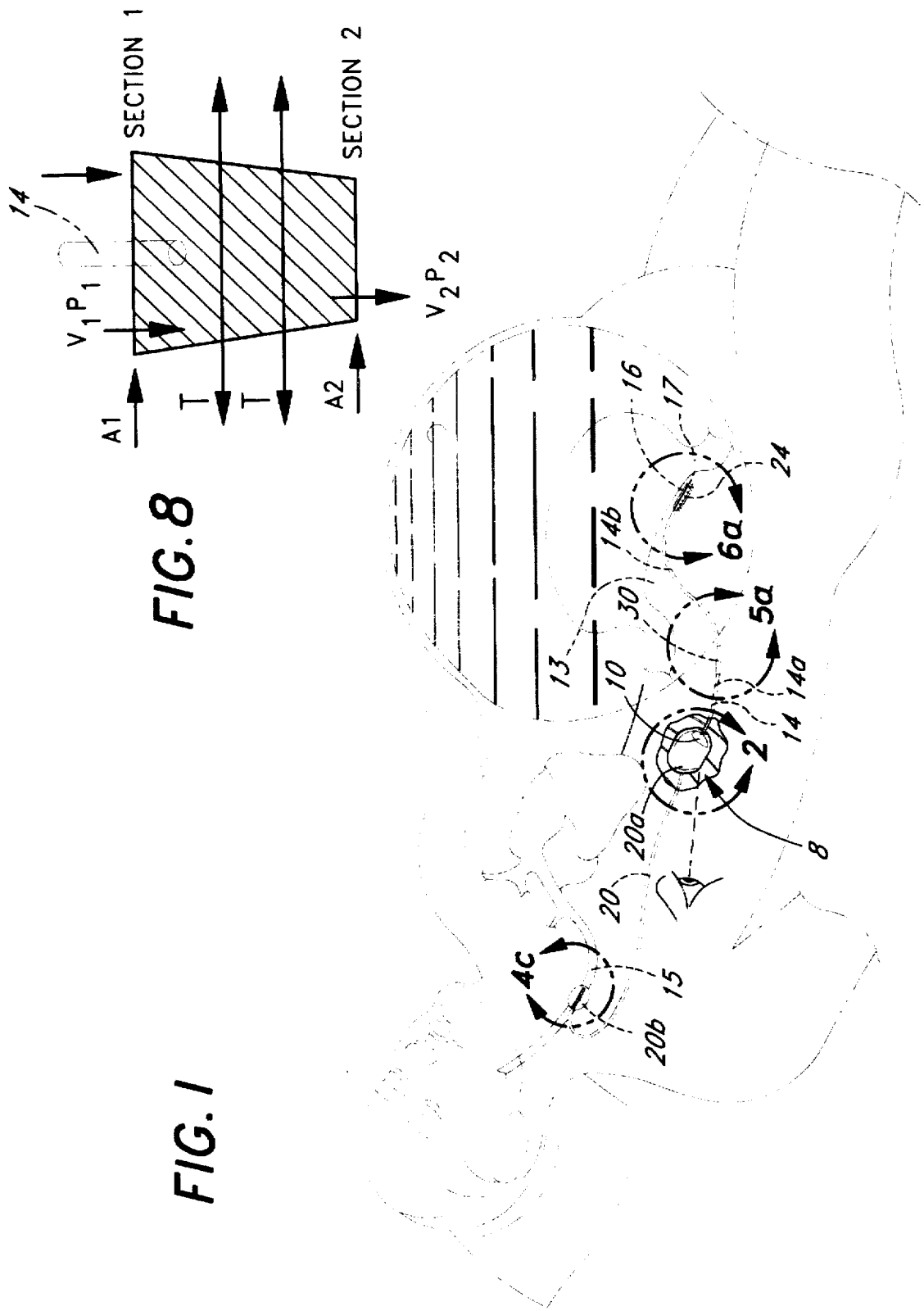
FIG. 1 is a perspective view of the medical valve of this invention showing the free end of the inlet tube implanted into the abdomen of a patient and the free end of the outlet tube implanted into the jugular vein of the patient.

As illustrated in FIG. 1, the medical device 8 of this invention is implanted under the skin 7 (FIG. 4a) of a patient, preferably in the abdominal region. It includes a one-way directional flow valve 10, a base plate 29 and a top cover 36. The base plate 29 and top cover 36 are bonded together using an adhesive to form an external shell 12 which houses the valve 10. There is a reservoir 9 created by the interior space within the shell 12, with one end 20a of an outlet tube 20 in communication with the reservoir. The other end 20b of the outlet tube 20 is placed in the jugular vein 15 of the patient. There is an inlet tube 14 connected to the valve 10 which has a free end 16 which is open at its tip 17. The free end 16 of the inlet tube 14 is placed in the abdomen 13 of the patient.

The valve 10 includes a bottom plate 1, a flexible, siliconized rubber membrane 2, and a top plate 3. The membrane 2 is originally in a non-folded condition and it has an hourglass-like shape narrowing at a central section and then expanding outwardly therefrom in both directions. The membrane 2 has a thickness ranging between 0.004 inches and 0.007 inches, preferably between 0.005 inches and 0.006 inches. There is an opening 5 in the membrane 2 in which the inlet tube 14 is inserted. An adhesive is used to bond the inlet tube 14 to the opening 5 of the membrane 2.

To assemble the valve 10, the membrane 2 is first folded as shown in FIG. 3c. Upon assembly of the valve 10, the overlapping edges 4 of the folded membrane 2 create between the two halves of the membrane 2 an internal chamber 31 (FIG. 3b) which has a trapezoidal configuration and a slit 6 (FIG. 3b) at the end of this chamber opposite the opening 5. In response to a predetermined pressure within the chamber 31, fluid will pass through the slit 6. Tension is applied to the overlapping edges 4 to maintain the slit 6 in a normally closed state. This enables the valve 10 to function as a one-way directional flow device. To create this tension, the folded membrane 2 is stretched and placed between the top plate 3 and the bottom plate 1 to hold the stretched membrane in tension. Next, the folded membrane 2 is placed between precisely aligned and spaced apart top plate 3 and bottom plate 1. These plates, with the membrane 2 stretched and sandwiched between them, are pressed together and interlocked by pins 39a, 39b, 39c, and 39d in the bottom plate 1 which pass through holes 40a, 40b, 40c, and 40d in the membrane 2 and bores 41a, 41b, 41c, and 41d in the top plate 3. Grooves 44a and 44b in the bottom plate 1 and fingers 45a and 45b in the top plate 3 interlock and clamp the folded membrane 2 firmly between the top plate 3 and the bottom plate 1. By varying the depth of the fingers 45a and 45b in the grooves 44a and 44b, the tension of the membrane may be varied. Ultrasonic welding is used to bond the bottom plate 1 and the top plate 3 together. The valve 10 is assembled with the inlet tube 14 affixed to the membrane 2.

The top cover 36 and the base plate 29 have a generally oval shape and are made of a flexible material such as, for example, siliconized rubber. The top cover 36 and the base plate 29 are made separately by injection molding. The top cover 36 is molded to be dome shaped. As best depicted in FIGS. 3d and 3e, there are opposed, semi-circular, molded openings 48a and 48b, respectively, at the forward end 49 and the rear end 50 along the outside edge 35 of the top cover 36. The base plate 29, which is generally flat, is surrounded by a raised rim 42 which has an upper edge 43. There are opposed, semi-circular, molded openings 48c and 48d, respectively, at the forward end 18 and the rear end 19 along the rim 42 of the base plate 29.

The valve 10 is positioned between the top cover 36 and the base plate 29 and then these components are assembled. As best shown in FIG. 3d, an end portion 11 of the inlet tube 14 is wedged between the semi-circular opening 48a in the top cover 36 and the semi-circular opening 48c in the base plate 29. As best shown in FIGS. 3e, 4a and 4b, an end portion 23 of the outlet tube 20 is wedged between the semi-circular opening 48b in the top cover 36 and the semi-circular opening 48d in the base plate 29. The top cover 36 and the base plate 29 are positioned so that the edge 35 of the top cover 36 and the edge 43 of the base plate 29 abut. These edges 35 and 43 are glued together to create the reservoir 9 within the shell 12. The top cover 36, the base plate 29, the inlet tube 14 and the outlet tube 20 are held in place with an biocompatible adhesive.

FIG. 1 and FIGS. 5a through 5d illustrates the telescoping feature of the inlet tube 14. The inlet tube 14 has two segments 14a and 14b. These segments 14a and 14b are nested within ends 30a and 30b of a telescopic housing 30. This feature allows the inlet tube 14 to elongate on demand without the need for surgical replacement.

In the free end 16 of the inlet tube 14, there are a number of parallel rows of aligned holes 24 in the end of the segment 14b that facilitate the draining of fluid from the abdomen. Parallel rigid fins 26 are between these rows of holes 24. As best illustrated in FIGS. 6a through 6d, the rows of holes 24 and the fins 26 are generally parallel to the longitudinal axis of the inlet tube 14. FIGS. 6c and 6d illustrate different configurations of rigid fin 26 structures with variations in numbers of fins. As best depicted in FIG. 7, the rigid fins 26 prevent naturally occurring omentum 21 from blocking the inlet tube 14. The omentum 21 comprises strands 21a of material which are supported by the fins 26 in an open structure. These rigid fins 26 assist in directing abdominal omentum 21 away from the open end and the holes, thereby minimizing blockage or clogging of the holes to allow fluid to flow through the open structure.

In response to elevated intra-abdominal pressure, fluid enters the holes 24 of the inlet tube 14 and flows through the inlet tube into the valve 10. The fluid fills the valve chamber 31, causing the pressure within the chamber to increase. When the pressure exceeds 10 millimeters of mercury (mm Hg), it causes the slit 6 in the folded membrane 2 to part, permitting the excess fluid to flow into the reservoir 9 of the shell 12. When the intra-abdominal pressure is reduced to between 8 and 10 mm Hg, the pressure is insufficient to cause the parting of the slit 6. This allows the valve 10 to operate as a check valve, preventing fluid flow from the reservoir 9 to the abdomen.

FIGS. 4a and 4b how the medical device 8 responds differently when manual pressure is applied. If the device 8 is not blocked, the user simply presses the shell 12 through the skin 7, compressing the shell to force fluid from the reservoir 9. As fluid once again enters the reservoir 9 through the valve 10, the reservoir is refilled with fluid. This feature permits the device to serve as a flush pump for the patient. In other words, the user may repeatedly depress the shell 12 to flush fluid from the reservoir 9, allow the reservoir to refill due to the intra-abdominal pressure, and once again depress the shell.

One highly desirable feature of the invention is the response of the shell 12 to manual pressure when the device 8 is blocked. The condition of the shell 12 serves as a way to detect blockage of the medical device 8. Both FIGS. 4a and 4b depict the response of the shell when the medical device 8 is blocked. FIG. 4a shows resistance of the shell 12 to manual pressure, indicating a blockage in the outlet tube 20, prohibiting the free flow of fluid from the reservoir 9. When there is a blockage in the inlet tube 14, manual pressure applied to the shell 12 produces a compressed shell (FIG. 4b) which remains in this compressed state even after discontinuing manual pressure. This compressed condition of the shell 12 is seen by the user as a contraction, dimpling, or depression of the shell.

Unique Flow Characteristics of the Valve

Most of the existing designs of valves used in the human body create a resistance in the path of the flow. Many times the need to have a variable flow valve is necessary.

The valve 10 provides a venturi because of its trapezoidal configuration which makes the valve a variable pressure valve. This can be demonstrated by using Bernoulli's Equation. Referring to FIG. 12, taking at the inlet a section Section 1 of the valve 10, there is a large area A1, the fluid velocity is $V_1$ and pressure is $P_1$; and taking at the outlet another section Section 2 of the valve 10, there is is a smaller area $A_2$, the fluid velocity is $V_2$ and the pressure is $P_2$.

Since the fluid that is coming into any part of Sections 1 and 2 is incompressible, whatever fluid comes into any section at unit time must leave that same section in unit time. This is the Theorem of Continuity. The membranes that make up this trapezoidal section are in tension created by the fingers 45a and 45b; the tension here is shown as T. Over the entire cross-sections, this tension is constant. The variable area of the sections of the valve makes this a serf-controlling, self-adjusting valve with no external means required to change the flow or pressure.

Writing the Bernoulli's Equation between Section 1 and Section 2:

$$\frac{P_1}{W} + \frac{V_1^2}{2g} + Z_1 = \frac{P_2}{W} + \frac{V_2^2}{2g} + Z_2$$

where $P_1$ is inlet pressure
$P_2$ is outlet pressure
$V_1$ is inlet velocity
$V_2$ is outlet velocity
W is weight of fluid
g is acceleration due to gravity
$Z_1$ and $Z_2$ are static pressures from the datum. In this particular case, $Z_1=Z_2$ Taking all the pressure and velocity terms on one side of the equation, we get:

$$\frac{P_1}{W} - \frac{P_2}{W} = \frac{V_2^2}{2g} - \frac{V_1^2}{2g}$$

$$\frac{P_1 - P_2}{W} = \frac{V_2^2 - V_1^2}{2g}$$

$$P_1 - P_2 = \frac{W}{2g}[V_2^2 - V_1^2]$$

Since W/2 g is a constant $P_1-P_2 \alpha V_2^2-V_1^2$

In other words, a very small difference in pressure between any two sections of the trapezoid leads to a greater flow. To explain this further, assuming $P_1=10$ mm Hg, $P_2=5$ mm Hg. $V_1=5$ μl/min and $V_2=10$ μl/mt.

$$P_1 - P_2 \quad \alpha \quad V_2^2 - V_1^2$$
$$10 - 5 \quad \alpha \quad 10^2 - 5^2$$
$$5 \quad \alpha \quad 100 - 25 = 75$$

For a small pressure difference of 5, the velocity difference becomes 75. Now if $P'_1$ became 15 and $P'_2$ 10 and $V'_2$ 15 and $V'_1$ 10.

$$P'_1 - P'_2 \quad \quad V_2^2 - V_1^2$$
$$10 - 5 \quad \quad (15)^2 - (10)^2$$
$$5 \quad \alpha \quad 225 - 100$$
$$5 \quad \quad 125$$

For a difference of pressure of 5, the velocity difference is now 125. This demonstrates that the trapezoidal configuration providing a venturi for the valve 10 helps to change automatically the fluid flow characteristics of the valve without having to make any physical adjustments.

SCOPE OF THE INVENTION

The above presents a description of the best mode contemplated of carrying out the present invention, and of the manner and process of making and using it, in such full, dear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiment disclosed. On the contrary, the intention is to cover all modifications and alternate constructions coming within the spirit and scope of the invention as generally expressed by the following claims, which particularly point out and distinctly claim the subject matter of the invention.

I claim:

1. A medical device for treating a patient suffering from ascites, including
   a valve having a membrane which forms a slit-like opening, said membrane having an aperture therein,
   said valve being formed, at least in part, by a pair of plates, which maintain the membrane in tension,
   a flexible shell which encloses the valve, said shell having a reservoir and first and second ends, with said first and second ends having openings therein,
   an inlet tube in communication with the valve through the aperture, said inlet tube having an end portion received by the opening at the first end of the shell, and a free end adapted to be inserted into the abdomen of a patient, and
   an outlet tube having one end in communication with the reservoir of the shell, said outlet tube having one end portion received by the opening at the second end of the shell and a free end adapted to be insert into the jugular vein of the patient.

2. The medical device of claim 1 where the shell is molded.

3. The medical device of claim 1 where the membrane is folded to form the slit-like opening.

4. The medical device of claim 1 where the membrane is formed into a chamber having a trapezoidal configuration.

5. The medical device of claim 1 where the shell expands or contracts in response to pressure.

6. The medical device of claim 1 where the valve is a one-way flow device.

7. The medical device of claim 1 where the free end of the inlet tube is open and there are a plurality of holes the free end.

8. The medical device of claim 7 where the free end of the inlet tube includes a rigid fin structure.

9. The medical device of claim 1 wherein the free end of the outlet tube is open.

10. The medical device of claim 9 where adjacent the free end there are a plurality of holes.

11. The medical device of claim 1 where the inlet tube has a telescoping section.

12. The medical device of claim 1 wherein the flexible shell responds to manual pressure.

13. The medical device of claim 1 where the shell is generally of an ovoid configuration.

14. The medical device of claim 1 where the shell is compressed when external pressure is applied to said shell.

15. The medical device of claim 14 where the shell resists compression when said outlet tube is blocked.

16. The medical device of claim 14 where the shell remains compressed when said inlet tube is blocked.

17. A medical device for draining fluids including a flexible shell,
   an inlet tube having a first end in communication with fluid and a second end received in the shell, a rigid fin structure at the first end of the inlet tube, a one-way directional flow device housed within said shell and in communication with the second end of the inlet tube, said one-way directional flow device having a pair of overlying membranes in tension which provide a slit-like opening, a fluid chamber reservoir within said shell said reservoir serving to collect drained fluid exiting the one-way directional flow device through the slit-like opening, and an outlet tube in communication with the second end of said shell.

18. The medical device of claim 17 where the one-way directional flow device is formed, at least in part, by plates holding in tension the membrane.

19. The medical device of claim 17 where the shell is compressed when external pressure is applied to said shell.

20. The medical device of claim 17 where the shell resists compression when said outlet tube is blocked.

21. The medical device of claim 17 where said shell remains compressed when said inlet tube is blocked.

22. The medical device of claim 17 where the inlet tube has a telescoping section.

23. The medical device of claim 1 where the membrane is formed into a chamber having a trapezoidal configuration.

24. A method for treating ascites by draining the fluid from the peritoneal or abdominal cavity of a patient, including the steps of (a) providing a medical device, including
   a valve having a membrane which forms a slit-like opening, said membrane having an aperture therein,
   a flexible shell which encloses the valve, said shell having a reservoir and first and second ends, with said first and second ends having openings therein,
   an inlet tube in communication with the valve through the aperture, said inlet tube having an end portion received by the opening at the first end of the shell, and a free end adapted to be inserted in the abdomen, and
   an outlet tube in communication with the reservoir, said outlet tube having one end portion received by the opening at the second end of the shell, and a free end adapted to be inserted into the patient's jugular vein.

(b) attaching the medical device to the patient with the flexible shell facing in a direction which allows said shell to be depressed, (c) inserting the free end of inlet tube into the abdomen to enable the ascites fluid to drain through the free end of the inlet tube, through the valve, and into the reservoir in the medical device, (d) inserting the free end of the outlet tube into the jugular vein of the patient to enable fluid to drain from the fluid reservoir into the heart.

25. The method of claim 24 where the valve includes a pair of plates holding the membrane in tension, with the membrane forming a chamber and the slit-like opening closing and opening in response to the internal pressure within the chamber, said pressure with the chamber increasing and decreasing as the fluid pressure varies.

26. The method of claim 24 where the shell is compressed when external pressure is applied to said shell.

27. The method of claim 24 where the shell resists compression when said outlet tube is blocked.

28. The method of claim 24 where the shell remains compressed when said inlet tube is blocked.

29. The method of claim 24 where the shell is depressed and then allowed to refill, repeating these steps of depressing and refilling to use the medical device as a pump to maximize the removal of ascites fluid from the abdomen.

* * * * *